(12) United States Patent
Waguespack (10) Patent No.: US 7,570,018 B2
(45) Date of Patent: Aug. 4, 2009

(54) RECHARGEABLE POWERED DEVICE

(75) Inventor: Kenneth Waguespack, North Brunswick, NJ (US)

(73) Assignee: Colgate-Palmolive Co., New York, NY (US)

( * ) Notice: Subject to any disclaimer, the term of this patent is extended or adjusted under 35 U.S.C. 154(b) by 221 days.

(21) Appl. No.: 11/050,674

(22) Filed: Feb. 7, 2005

(65) Prior Publication Data

US 2006/0176017 A1    Aug. 10, 2006

(51) Int. Cl.
    H02J 7/00    (2006.01)
(52) U.S. Cl. .................. 320/113; 320/114; 320/115
(58) Field of Classification Search ............... 320/120, 320/113, 110, 132, 114, 115
    See application file for complete search history.

(56) References Cited

U.S. PATENT DOCUMENTS

| | | | | |
|---|---|---|---|---|
| 4,743,831 | A | * | 5/1988 | Young ................... 320/127 |
| 6,611,780 | B2 | * | 8/2003 | Lundell et al. .......... 702/122 |
| 6,709,784 | B2 | * | 3/2004 | Resch et al. ............ 429/123 |
| 2003/0231001 | A1 | * | 12/2003 | Bruning .................. 320/108 |
| 2005/0024011 | A1 | * | 2/2005 | Chen ..................... 320/107 |

FOREIGN PATENT DOCUMENTS

| | | |
|---|---|---|
| DE | 195 13 539 A1 | 10/1996 |
| DE | 19513539 A1 | 10/1996 |
| DE | 103 18 748 A1 | 11/2004 |
| JP | 08 088942 A | 4/1996 |
| JP | 2000 245072 | 9/2000 |
| WO | WO 96/09019 A1 | 3/1996 |
| WO | WO 97/08804 A | 3/1997 |
| WO | WO 97/08804 A1 | 3/1997 |
| WO | WO2005/043709 A | 5/2005 |
| WO | WO 2005/043709 A1 | 5/2005 |

\* cited by examiner

*Primary Examiner*—Akm E Ullah
*Assistant Examiner*—Nguyen Tran
(74) *Attorney, Agent, or Firm*—Amy M. Fernandez (57) ABSTRACT

A rechargeable device is provided having a motor and a small-capacity battery coupled to the motor. The small-capacity battery has a storage capacity sufficient for an average use of the device up to a few average uses of the device. A charger may also be provided for charging a rechargeable device. The charger may have charging circuitry and an indicator indicating a recharge state of the rechargeable device. The charger may have a large-capacity battery with a storage capacity greater than a small-capacity battery of the rechargeable device. The large-capacity battery provides sufficient electrical power to recharge the small-capacity battery. The charger may also have a power cord for receiving power from an alternating current power source. Methods for using a rechargeable device and for charging a rechargeable device are also provided.

7 Claims, 6 Drawing Sheets

PRIOR ART

RECHARGEABLE POWERED DEVICE

FIELD OF THE INVENTION

The present invention relates to a rechargeable powered device. In particular, the present invention relates to a rechargeable powered device having a small-capacity, quickly-rechargeable battery, such as a quickly-rechargeable powered toothbrush, and to a charging unit for charging the device.

BACKGROUND OF THE INVENTION

Powered toothbrushes have been available for some time. Powered toothbrushes have advantages over manual (non-powered) toothbrushes in that they impart movement to the bristles at much higher speeds than possible manually, and may impart different types and directions of motion. These motions, generally in combination with manual movement of the toothbrush by the user, may provide superior cleaning than manual toothbrushes. Conventional powered toothbrushes are powered by disposable or rechargeable batteries that power an electric motor, which in turn drives the toothbrush head. The batteries of conventional powered toothbrushes are bulky standard-sized batteries that provide enough power for numerous (more than a few) average cleaning sessions without being replaced or recharged.

Figure 1:
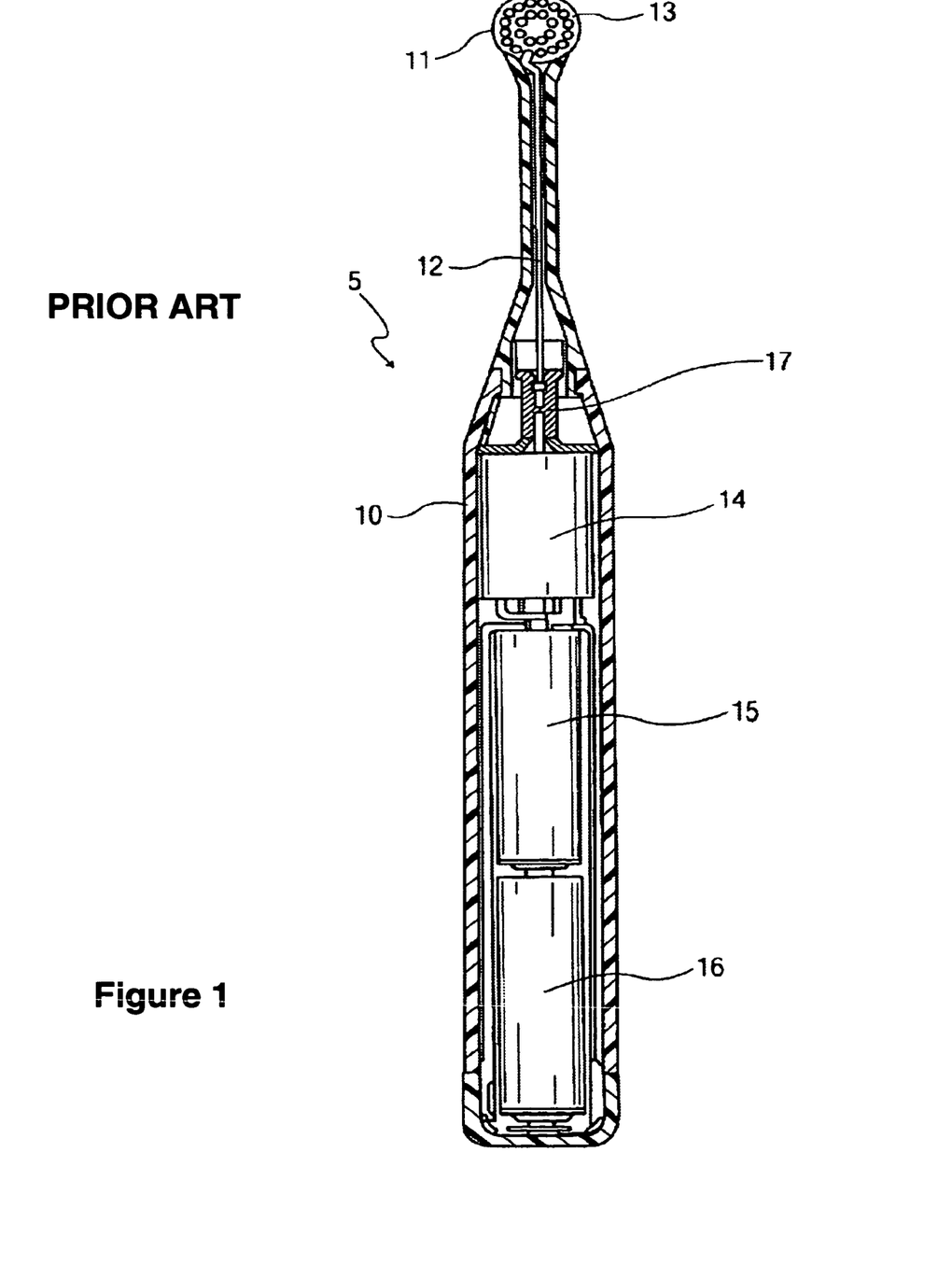
FIG. 1 is a cross-sectional view a conventional powered toothbrush.

FIG. 1 shows an example of a powered toothbrush as depicted in U.S. Pat. No. 6,813,793 to Eliav. The toothbrush 5 has a disc-shaped bristle carrier that is driven in a vibrating or oscillating manner along with bristles attached thereto. Toothbrush 5 has a handle portion 10 at a proximal end of the toothbrush and a head 11 at a distal end of the toothbrush. The handle portion 10 has compartments for containing a motor 14 and batteries 15 and 16. The head 11 includes a generally circular bristle holder 13. A rotatable shaft 12 extends from the motor 14 to the head 11. A shaft coupling 17 may be located along the shaft 12 and may be configured to provide for the shaft 12 to be separated at a point between the motor 14 and the head 11. This can permit the shaft to be removed from the toothbrush 5, e.g., for cleaning or replacement.

Batteries 15 and 16 of conventional powered toothbrushes are bulky, standard-sized batteries, such as AA size batteries. The batteries store sufficient power to operate motor 14 for numerous (more than a few) average cleaning sessions without requiring replacement batteries or without recharging the batteries.

SUMMARY OF THE INVENTION

Aspects of the present invention provide a rechargeable device having a motor and a small-capacity battery coupled to the motor. The small-capacity battery may have a storage capacity sufficient for an average use of the device up to a few average uses of the device.

Aspects of the present invention also provide a charger for charging a rechargeable device. In one construction, the charger indicates when the brush has sufficient power for at least one average use. The charger may have charging circuitry and an indicator indicating a recharge state of the rechargeable device. The charger may have a large-capacity battery with a storage capacity greater than a small-capacity battery of a corresponding rechargeable device to be charged by the charger. The large-capacity battery provides sufficient electrical power to recharge the small-capacity battery. The charger may also have a power cord for receiving power from an alternating current power source to recharge the small-capacity battery.

Other aspects of the present invention provide methods for using a rechargeable device and for charging a rechargeable device. These and other aspects are addressed in relation to the figures and related description.

DETAILED DESCRIPTION OF THE INVENTION

Figures 2A, 2B:
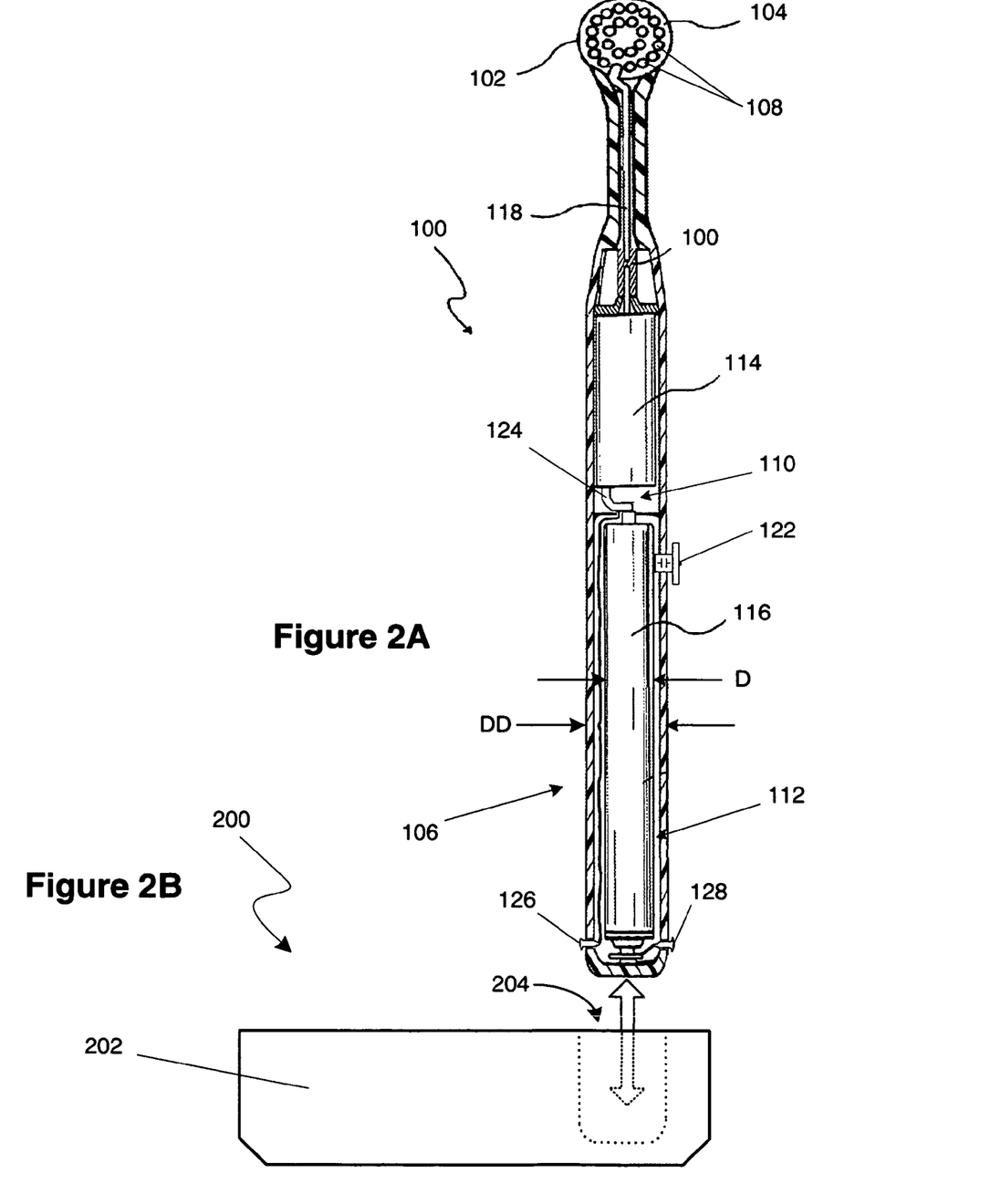
FIG. 2A is a cross-sectional view of a rechargeable powered toothbrush according to an embodiment of the present invention.
FIG. 2B is a cross-sectional view of a toothbrush charger that may be used with the toothbrush of FIG. 2A according to another embodiment of the invention.

A rechargeable powered toothbrush 100 is shown in FIG. 2A for supporting one or more aspects of the invention. It is understood, however, that aspects of the invention may be applicable to a wide variety of powered devices that can take advantage of a relatively quick recharging configuration, a relatively low-capacity battery configuration sufficient for one or a few uses, and/or a portable charging configuration. For example, aspects of the invention may be applicable to powered toothbrushes having one or more movable bristle carriers, one or more movable cleaning elements, and/or other powered sections (e.g., vibrating sections, electrically charged elements, pumping devices to pump a cleaning solution, etc.). Further, aspects of the invention may be applicable for a wide variety of other powered devices. For instance, powered brushes such as shoe polishers, powered grooming devices such as nose-hair clippers or nail clippers, powered food-preparation devices such as can openers or hand mixers, and other powered devices may take advantage of aspects of the invention.

In the example embodiment of FIG. 2A, a rechargeable powered toothbrush 100 has a head portion 102 at one end supporting a movable bristle carrier 104, and a handle portion 106 at the opposite end. The handle portion 106 has one or more compartments 110 and 112 for containing a powered motor 114 and a battery 116. The motor 114 is operatively connected to the movable bristle carrier 104, such as by a rotatable shaft 118 extending from the motor to the head portion. The motor may drive the movable bristle carrier in various ways, such as by vibrating, rotating or oscillating it along with bristles 108 attached thereto. Further, other powered toothbrush configurations are contemplated in which the motor drives the bristles to vibrate, lift or otherwise move without the use of a movable carrier. For example, the toothbrush may vibrate as disclosed in U.S. Pat. No. 6,802,097 to Häfliger et al., which is incorporated herein by reference.

As shown, toothbrush 100 includes a neck portion 120 connecting the handle portion and the head portion, which also supports the shaft 118. The neck 120 may be configured to be separated at a point between the motor and the head portion. This can permit the head portion to be removed from the toothbrush for interchangeability with other head portions, for cleaning and for replacement, etc.

Motor 114 is electrically connected with battery 116 and a switch 122. It may also be connected to optional control apparatus (not shown). For example, battery charging circuitry may be included to control the recharge rate of the battery, or speed control circuitry may be used to provide the user with several speed options. The motor 114, battery 116 and switch 122 are connected in series, with the positive pole of the battery being connected to the motor via a spring lead 124. The negative lead of the battery is connected to the motor through switch 122 (negative lead connection to the motor is not shown). Charging connectors 126 and 128 extend through a bottom region of handle portion 106 for receiving an electrical charging input. Respective ones of the connectors 126, 128 are connected directly to one of the leads for battery 116. They may also be connected to battery charging circuitry (not shown), which may be connected to the battery for controlling the recharge rate of the battery and/or to reduce the possibility of overcharging or otherwise damaging the battery.

Although battery 116 is shown as a single unit, it is understood that the battery may include a single unit or a plurality of primary and/or secondary units or cells arranged in parallel, in series or in a combination thereof. Further, it is understood that the term "battery" as used herein means a device that stores electrical energy, converts stored energy into electrical energy and/or generates electrical energy. For example, the term battery may include a capacitor, a bank of capacitors, a condenser or a bank of condensers, which store electric potential. In another example, the term battery may include a dry chemical cell(s), such as a conventional alkaline battery, or may include a wet cell(s), such as a conventional lead-acid cell battery, which convert energy stored in a chemical form into electrical energy. In a further example, the term battery may include a fuel cell that generates electrical energy via a chemical process between a fuel (e.g., hydrogen) and an oxidant.

Motor 114 is a conventional DC motor, which, for example purposes, is adapted to operate with a 3-4 volt power source. For normal uses of the toothbrush, the motor provides about 1 ounce-inch of torque, rotates about 3,000 revolutions per minute, and draws about 200 milliamps of current. It is understood that the motor could have a variety of torques and speeds depending on the desired configuration and that could operate with a variety of power sources. For example, motor 114 may be adapted to operate with a power source of about 3 volts to about 12 volts. It may provide torque of about one to 10 ounce-inches of torque, rotate about 2,000-5,000 revolutions per minute, and draw about 10 to 100 milliamps of current.

It is further understood that alternate configurations for motor 114 and example embodiment 100 are possible that have a broad range of performance characteristics, which may be greater or less than that of conventional powered toothbrushes. For instance, a small torque motor may be appropriate for toothbrush configurations in which the bristles lift or vibrate rather than rotate, or a large torque motor may be appropriate for toothbrush configurations in which multiple bristle sections move simultaneously. In an alternate example toothbrush configuration that applies an electrical charge in a user's mouth without moving bristle sections, the motor may be omitted completely and the battery may be used to provide the electrical charge.

For example embodiment 100, battery 116 is a rechargeable battery that is adapted to be charged relatively quickly and to provide a relatively consistent output voltage. As noted above, battery 116 may be a plurality of batteries or battery cells connected in series and/or in parallel, as needed, to provide a desired voltage and storage capacity. Further, battery 116 may make use of a variety of rechargeable battery technologies, either alone or in combination, such as nickel-cadmium, nickel-metal hydride, lithium ion, alkaline or other rechargeable battery technologies. For the example configuration of toothbrush 100, battery 116 is a nickel-metal hydride battery having three small, serially-connected, 1.2 volt cells (not shown), which each have an overall diameter of about 10 mm. Battery 116 provides a collective output of 3.6 volts and has a storage capacity of about 50 milliamp-hours. As such, battery 116 is able to drive motor 114 for about 15 minutes when fully charged based on the motor drawing about 200 milliamps of current (i.e., 50 milliamp-hour battery/200 milliamp current×60 minutes/hour).

Motor 114 and battery 116 are configured such that the battery is able to operate motor 114 for a few average uses or sessions of the toothbrush, which may each be about one to five minutes. As used herein, a single average use or session refers to a period or range of periods for operating the powered device, which is a normal period of a single use for most users of the particular type of device. For powered toothbrush 100, an average use is the period or range of periods for which most persons use a powered toothbrush to brush their teeth in a single brushing.

In one construction, toothbrush 100 is configured such that a single average use is provided by less than a full charge of the battery. Only about 10% to 30% of battery 116 is required for the example configuration of toothbrush 100 in order to power it for a single average use. Small capacity battery 116 at its full capacity of 50 milliamp-hours can drive motor 114 for about 15 minutes, which is about three or more average uses of the toothbrush. Moreover, battery 116 can provide power for an average use of about one to 5 minutes when the battery is charged to about ⅓ of its storage capacity.

It is understood that many other configurations are possible that can permit the respective powered device to operate for a single use up to a few uses when fully charged. For instance, a range of less-fully charge battery states may power the respective device for an average single use, such as about 10% to 90% of the battery storage capacity. For instance, in a low capacity configuration, the battery may provide for a single use of the device based on a substantially full charge, which may about 90% to 95% of its capacity. In an extended use configuration, about 70% to 90% of its storage capacity may power a single use with additional capacity for powering an extended use. In a moderate capacity configuration, the battery may have sufficient capacity to power the respective device for a few uses when the battery is fully charged. In a high capacity configuration of toothbrush 100, the toothbrush may be able to operate for several uses (e.g., about 4 to 6 average uses) when fully charged. Such a higher powered configuration may be advantageous for a toothbrush having interchangeable head portions 108 for use with multiple users. As such, a single charge permits a few users to operate the toothbrush substantially continuously over a short period without recharging it between uses by the different users.

In general, however, battery 116 is a relatively small capacity battery that has the advantage of being quickly rechargeable to full capacity, and/or being quickly rechargeable to a less-than full capacity sufficient for a single use or for a few uses. Thus, a user can have the toothbrush quickly recharged enough to permit it to be used within a short period. The relatively small capacity of battery 116 permits it to be recharged quickly to its full capacity in comparison with conventional, large-capacity batteries. In addition to its small capacity, the recharge rate of battery 116 can be further improved by providing a high charging current in comparison with the current requirements of the motor. For instance, providing a high recharge current of about 1000 milliamps to battery 116, which is significantly higher than the 200 milliamp current provided by battery 116 to motor 114 during operation, will substantially charge the battery in about 4.5 minutes. This assumes a recharge factor of about 1.5 for the battery and charger configurations. If battery 116 has a capacity of about 50 milliamp hours and if the recharge current is about 1000 milliamps, the ideal recharge time would be about 0.05 hours (50 milliamp hours/1000 milliamps) or about 3 minutes. With the assumption of a 1.5 recharge factor, the estimated recharge time drops to around 4.5 minutes. Thus, motor 114 in the example configuration can operate toothbrush 100 for about 15 minutes on a single charge of battery 116, and the battery can be recharged in about 4.5 minutes.

Battery 116 is also rechargeable within a shorter period such that it has a capacity sufficient for a single use. For instance, battery 116 can be recharged to about 34% capacity (i.e., about 17 milliamp hours) in about one-third of the amount of recharge time (i.e., about 1.5 minutes) of a full recharge. Thus, in a little more than one minute, toothbrush 100 can be sufficiently charged to provide the user with a single average use.

Toothbrush 100 is a small, lightweight powered toothbrush that is comparable in size and weight to a conventional manual toothbrush. This is largely due to the small-capacity, quickly-rechargeable battery 116, that is relatively small and lightweight compared with conventional disposable batteries and rechargeable batteries. The small size and weight may be desirable for many users, and provides cost savings associated with savings in toothbrush materials. For instance, if battery 116 has a 7 mm diameter, which is almost a 50% reduction in size from a standard AA battery (about 14.5 mm diameter), toothbrush 100 may have an overall size reduction of about 20% to 40% compared with a conventional powered toothbrush using an AA-sized battery or a pair of axially aligned AA-sized batteries. As many conventional powered toothbrushes include a pair of AA-sized batteries disposed side-by-side, the weight and size reduction may be even more substantial. The outer diameter DD of toothbrush 100 shown in FIG. 2A at handle portion 106 may be about 10 mm, which is about the size of a manual toothbrush handle. It is contemplated that other handle sizes are possible based on the battery size and arrangement. For instance, battery 116 may have a diameter D of about 5 mm to about 13 mm, or more particularly about 10 mm. Various sizes of toothbrush handles that are smaller than conventional powered toothbrushes may be provided via the use of smaller-diameter batteries in various arrangements, such as a linear arrangement.

Figure 2C:
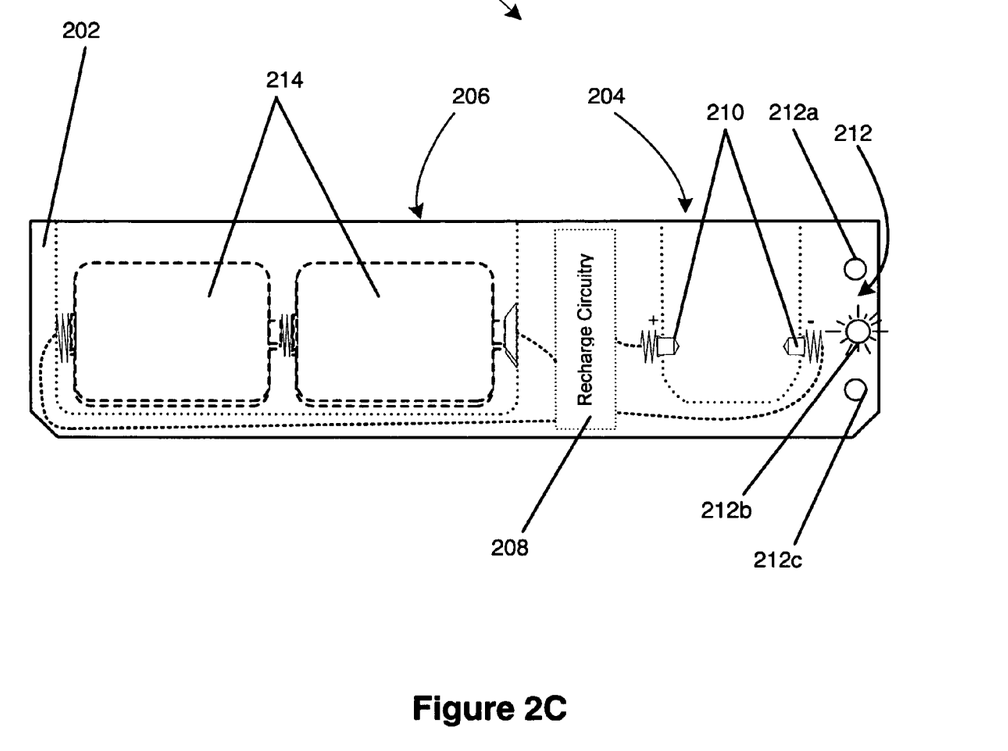
FIG. 2C is a side view of the toothbrush charger of FIG. 2B showing functional aspects of the charger.

Referring now to FIGS. 2B and 2C, a charger 200 is generally shown according to an embodiment of the invention. Charger 200 is a combination charger/holder unit that recharges toothbrush 100, as well as holds it during storage. It is understood that various embodiments of charger 200 are possible that cooperate with other powered devices and that may not store the respective powered device. As illustrated in FIG. 2B, charger 200 includes a base unit 202 having a cradle 204 formed at a top portion of the base unit. The cradle is adapted to receive an end region of handle portion 106 for supporting toothbrush 100 while it is being stored between uses.

As shown in FIG. 2C, charger 200 may be a portable, battery-operated unit. As such, charger 200 includes a battery compartment 206 formed in the base unit 202, recharge circuitry 208, and charging contacts 210. It may also include charging indicators 212. Battery compartment 206 is configured to accept one or more replaceable batteries 214. The battery-operated unit provides a portable charger/toothbrush combination, which can take advantage of the benefits of lightweight toothbrush 100 while retaining the advantages of a portable system.

Batteries 214 provide a power source for recharging the toothbrush 100. The batteries are conventional disposable batteries, such as D-sized batteries, and/or rechargeable batteries. They may also include an alternative portable power supply, such as a fuel cell, for providing electric power. As shown, charger 200 is configured to operate using four standard-sized batteries, such as D-size batteries, which provide a power source for charger 200. The D-sized batteries provide about 1.5 volts of output each, and are serially-connected to provide about 6 volts of output collectively. The storage capacity for the D-size batteries is about 12,000 milliamp hours, which is a large capacity in comparison with the small-capacity battery 116 used in powered toothbrush 100. A fresh set of D-size batteries 214 storing 12,000 milliamp hours of power can charge small-capacity battery 116, which has a capacity of about 50 milliamp hours, about 240 times (i.e., 12,000 milliamp hours/50 milliamp hours). The estimation of 240 recharges assumes a 25% loss in the recharging process, as the four batteries 214 provide about 6 volts of electricity to charge the 4.5 volt, small-capacity battery 116.

As shown in FIG. 2C, batteries 214 may be connected to recharge circuitry 208, which may optionally be located in toothbrush 100. Recharge circuitry 208 includes conventional recharge circuitry that controls the rate at which the rechargeable batteries are recharged, and which could include a microcontroller (not shown) for controlling the charging process. For instance, recharge circuitry 208 may initially provide a high current for a rapid recharge of batteries 116 according to instructions from the microcontroller, and then reduce the current to provide a trickle charge for longer-term storage of toothbrush 100 within charger 200. Recharge circuitry may also alter the charging current as needed to reduce memory effects on battery 116 or to otherwise improve the charging process or to protect apparatus or persons. It may also cease to charge batteries 116 to avoid overcharging them or to avoid an unsafe condition.

As shown in FIG. 2C, charging contacts 210 are electrically connected to recharge circuitry 208. The charging contacts are adapted to make electrical contact with charging connectors 126 and 128 on toothbrush 100. As shown, charging contacts 210 are spring-loaded pins that are biased toward contact with charging connectors 126 and 128 while toothbrush 100 is stored within the charger. Other recharging embodiments are also contemplated for use with the present invention, such as a primary coil in charger 200 that recharges batteries 116 of a powered device by inducing a current in a secondary coil of the powered device. Thus, direct electrical contact between the charger and the powered device may not be required to recharge the powered device.

As shown, charger 200 includes indicators 212 that provide charging status or other information to the user. For instance, a first indicator 212*a* flashes or lights up to indicate that toothbrush 100 does not have a sufficient charge for a single use. A second indicator 212*b* flashes or lights up to indicate that toothbrush 100 has a sufficient charge for a single use. A third indicator 212*c* flash or lights up to indicate that toothbrush 100 has been substantially fully charged. Indicators 212 are connected to and controlled by recharge circuitry 208, which uses power from batteries 214 to light up the indicators. Recharge circuitry 208 evaluates the charging current accepted by powered device 100 to determine the amount of charge stored in its batteries 116. In other embodiments, circuitry within the powered device may evaluate the capacity condition of its batteries and provide such information to the charger, which may activate the appropriate indicator. Overall, the indicators inform the user of the recharge state of the respective powered device. For instance, if the user of toothbrush 100 places it in charger 200 when it has a substantially discharged battery 116, indicator 212a flashes or lights up to indicate a low charge condition. After battery 116 is charged for about one to one and a half minutes to about 34% of its capacity such that it can power the toothbrush for a single use, indicator 212b is activated to indicate that toothbrush 100 may be used for a single use. If the user continues to leave toothbrush 100 within charger 200, when battery 116 is substantially completely charged, indicator 212b ceases to flash or light up and indicator 212c then illuminates to indicate a fully charged condition.

Figure 3:
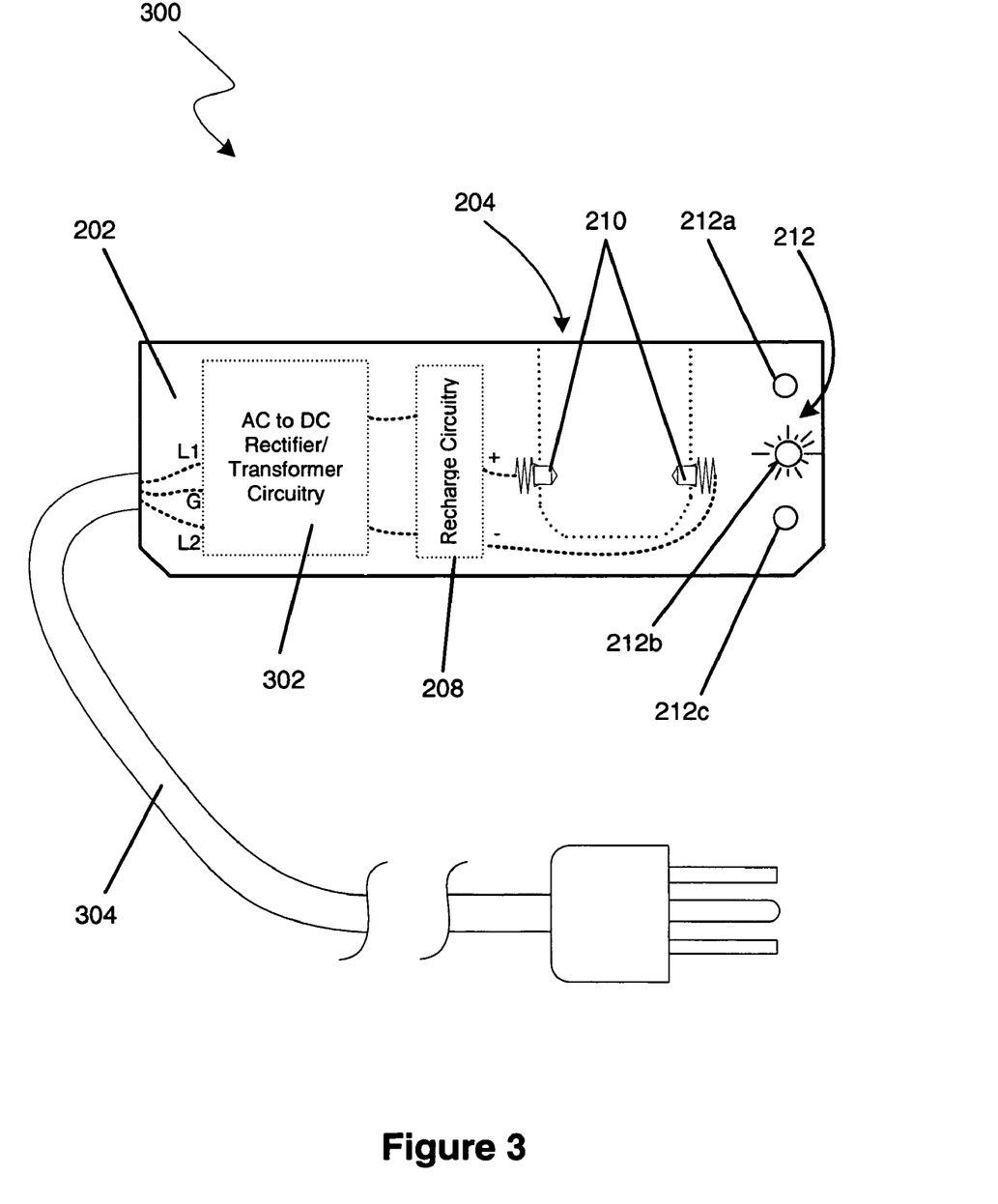
FIG. 3 is a side view of a toothbrush charger according to a further embodiment of the invention.

Referring now to FIG. 3, a charger 300 is shown according to another embodiment of the invention. Charger 300 generally includes the same aspects as charger 200, except as discussed below. As with charger 200, charger 300 may be used with toothbrush 100 or other powered rechargeable devices. Charger 300 differs from charger 200 in that it is powered by an alternating current power source rather than a direct current power source. As such, charger 300 includes an AC-to-DC rectifier/transformer circuitry 302 and an alternating current power cord 304, rather than battery compartment 206 with batteries 214. Although shown as logically separate entities, circuit 302 and recharger circuit 208 may be co-located in a single circuit.

Circuitry 302 is conventional rectifier circuitry, which rectifies alternating current electricity provided via cord 304 into a direct current output, and transforms it into an appropriate voltage for providing a charging current. Thus, charger 300 receives a conventional 110 volt alternating power supply and converts it to a 6 volt direct current power supply via circuit 302. In a manner similar to charger 200, recharge circuitry 208 then controls the direct current power supply as needed to recharge battery 116 of toothbrush 100.

In an alternate configuration (not shown), the charger may include the battery compartment 206 of charger 200 along with batteries 214, as well as circuitry 302 and power cord 304 of charger 300. Such a combination charger could operate as a unit plugged into an alternating current power supply, or as a portable battery-operated unit, according to the needs or desires of the user. Further, such a combination configuration could provide an operational unit in the event of alternating-current power outage.

Figure 4:
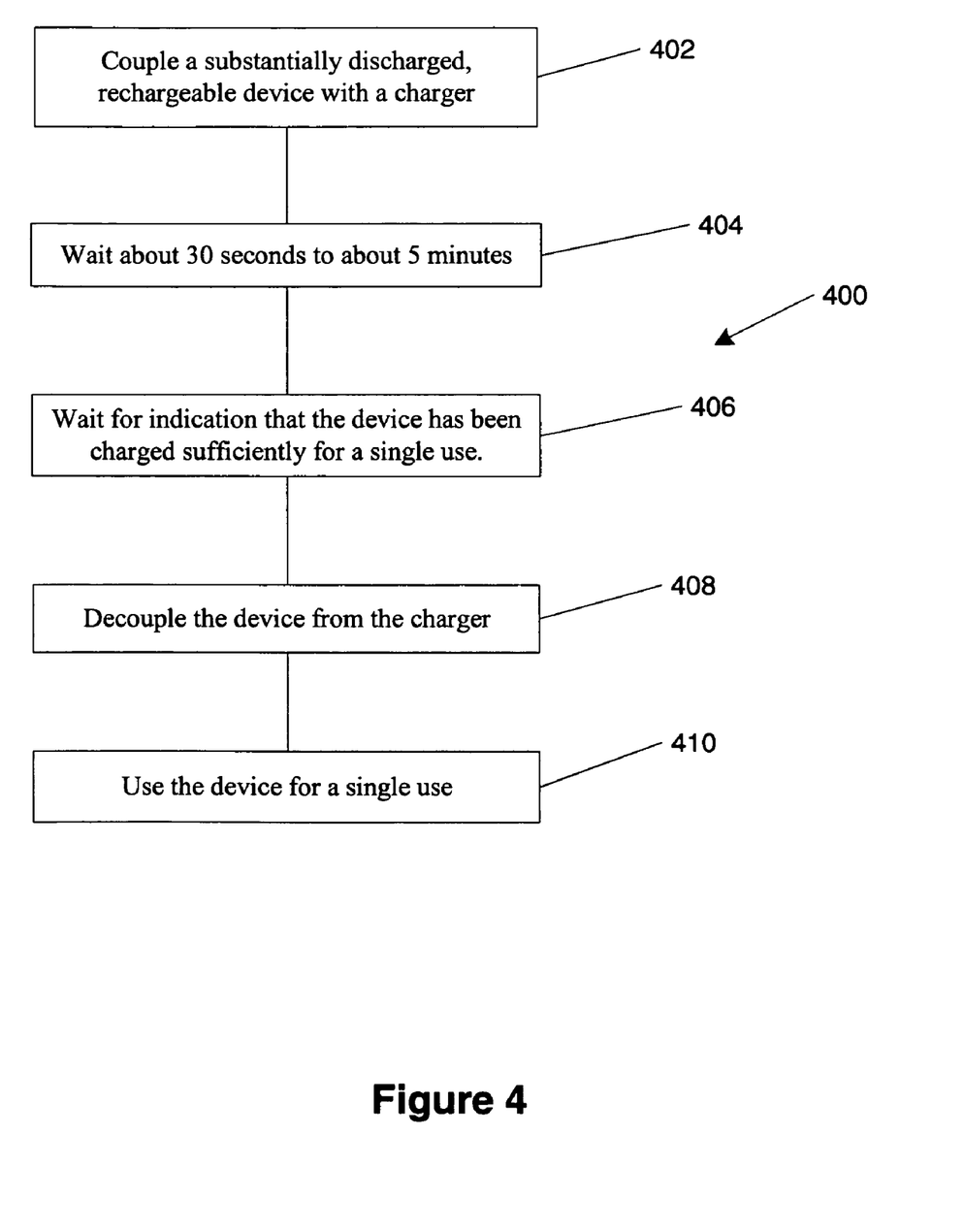
FIG. 4 is a flow diagram illustrating a method for using a rechargeable device according to an additional embodiment of the invention.

Referring now to FIG. 4, a method 400 is shown for using a rechargeable powered device, such as a powered toothbrush, according to an embodiment of the invention. Method 400 will be discussed using the example toothbrush 100 and charger 200 as discussed above. However, it is understood that method 400 may be practiced with a wide variety of rechargeable devices and charger units.

As shown, method 400 includes the step 402 of coupling a substantially discharged, rechargeable device into a charging configuration with a charger. For example, a user may place toothbrush 100 into a storage/charging configuration with charger 200. Another step 404 includes waiting a period between about 30 seconds and 5 minutes and/or performing the step 406 of receiving an indication that the rechargeable device is sufficiently charged for a single use of the device. For instance, the user waits about 30 seconds to about 5 minutes after installing toothbrush 100 into charger 200, and/or may see indicator 212b flashing to show toothbrush 100 has a charge sufficient for a single use. The user then performs the step 408 of de-coupling the rechargeable device from the charger and the step 410 of using the rechargeable device for a single use. For instance, the user may remove toothbrush 100 from charger 200 and proceed to brush his teeth. Method 400 may continue by repeating process as needed when the rechargeable device is substantially discharged.

Figure 5:
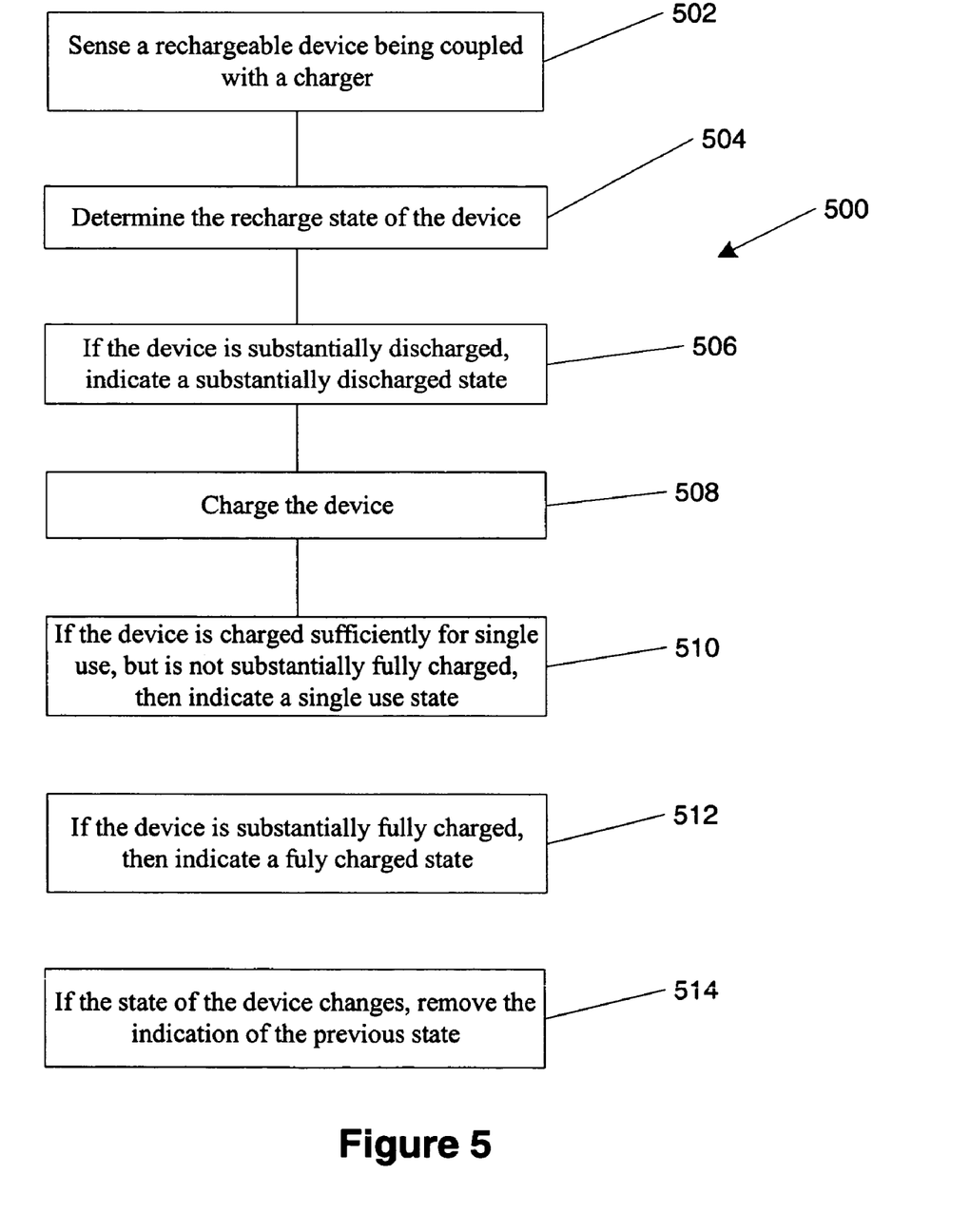
FIG. 5 is a flow diagram illustrating a method for recharging a rechargeable device according to a further embodiment of the invention.

Referring now to FIG. 5, a method 500 is shown for recharging a powered device, such as a powered toothbrush, according to a further embodiment of the invention. Method 500 will also be discussed using the example toothbrush 100 and charger 200. However, it is understood that method 500 may be practiced with a wide variety of rechargeable devices and charger units.

As shown, method 500 includes the step 502 of sensing a rechargeable device being coupled with a charger and the step 504 of determining the recharge state of the rechargeable device. For example, recharge circuitry may sense a connection between contacts 210 of charger 200 and connectors 126, 128 of toothbrush 100 when the toothbrush is placed in the charger. Recharge circuitry may further evaluate the recharge state of the battery 116 within toothbrush 100. This may be done, for example, by providing a maximum charging power supply to connectors 126 and 128, determining the voltage potential from batteries 214, and comparing the charging current accepted by toothbrush 100 with charging current curves for toothbrush 100. For instance, if toothbrush 100 draws a maximum current of 1000 milliamps when batteries 214 provide a full voltage of 6 volts, recharging circuitry may determine that batteries 116 are substantially discharged. These steps may be substantially performed by a microcontroller (not shown) within recharging circuitry 208. If the recharge state of the rechargeable device is determined to be substantially discharged, the charger then performs the step 506 of indicating a substantially discharged state and the step 508 of charging the rechargeable device. For example, charger 200 may flash indicator 212c to show that toothbrush 100 is substantially discharged and proceed to charge the toothbrush.

The charger may repeatedly perform the step 504 of determining the recharge state of the rechargeable device. If the charger determines that the rechargeable device has sufficient capacity for a single use, the charger performs the step 510 of indicating a state of being charged sufficiently for a single use. If the charger determines that the rechargeable device has been substantially fully charged, the charger performs the step 512 of indicating a state of being fully charged. If the charger has previously indicated the state of being substantially discharged or being charged sufficiently for a single use, the charging performs the step 514 of removing an indication of a previous state when it determines that the previous state has changed. As example, charger 200 may initially flash indicator 212c to signify a substantially discharged state, and then turn off indicator 212c and flash indicator 212b to signify toothbrush 100 has been charged sufficiently for a single use. As charging continues and toothbrush 100 becomes substantially charged, charger 200 may turn off indicator 212b and flash indicator 212a.

While the present invention has been described in connection with the illustrated embodiments, it will be appreciated and understood that modifications may be made without departing from the true spirit and scope of the invention. In particular, the invention may apply many different rechargeable devices, chargers, and/or methods for use the same.

What is claimed is:

1. A rechargeable powered toothbrush system comprising:
a rechargeable powered toothbrush having a motor and a rechargeable small-capacity battery coupled to the motor, the rechargeable small-capacity battery having a storage capacity sufficient for at least a single average use of the toothbrush and up to a few uses; and
a charger electrically coupled to the rechargeable powered toothbrush, the charger comprising
a holding unit for the rechargeable powered toothbrush and
a large-capacity battery having a comparatively larger storage capacity than the rechargeable small-capacity battery, the large-capacity battery configured for charging the small-capacity battery when the rechargeable toothbrush is coupled to the charger and being retained in a storage position in the holding unit,
wherein the charger further comprises an indicator indicating a state of the small-capacity battery, the state including a single use state when the small-capacity battery is charged with sufficient energy to power the rechargeable toothbrush for the single average use and a full charge state when the small-capacity battery is substantially fully charged to an energy level sufficient to power the rechargeable toothbrush for a plurality of the single average uses.

2. The rechargeable toothbrush system of claim 1, wherein the storage capacity of the large-capacity battery is two or more times greater than the storage capacity of the small-capacity battery.

3. The rechargeable toothbrush system of claim 1, wherein the storage capacity of the large-capacity battery is ten or more times greater than the storage capacity of the small-capacity battery.

4. The rechargeable toothbrush system of claim 1, wherein the storage capacity of the small-capacity battery when in the full charge state is sufficient for powering the toothbrush for up to five minutes and the system is configured to charge the small-capacity battery in a charging period within about 30 seconds to about 5 minutes from a substantially discharged state to the single-use state for operating the toothbrush for the single average use, the single-use state being less than the full charge state of the small-capacity battery.

5. The rechargeable toothbrush system of claim 1, wherein the storage capacity of the small-capacity battery when in the single use state has sufficient charge for powering the motor between about one to about five minutes, the single use state being less than the full charge state of the small-capacity battery.

6. The rechargeable toothbrush system of claim 1, wherein the storage capacity of the small-capacity battery when in th full charge state is sufficient for powering the motor between about one to about thirty minutes and the system is configured to charge the small-capacity battery within about 30 seconds to about 5 minutes from a substantially discharged state to the single use state for operating the toothbrush for the single average use, the single use state being less than the full charge state of the small-capacity battery.

7. The rechargeable toothbrush system of claim 1, wherein the small-capacity battery is selected from the group consisting of a capacitor, a nickel-metal hydride battery, a nickel-cadmium battery, a lithium-ion battery, and a rechargeable alkaline battery.

* * * * *